United States Patent [19]

Hall et al.

[11] Patent Number: 4,917,709
[45] Date of Patent: Apr. 17, 1990

[54] PERMEATION PH CONTROL SYSTEM

[75] Inventors: Randall C. Hall, College Station; Karl M. Williams, Bryan, both of Tex.

[73] Assignee: O. I. Corporation, College Station, Tex.

[21] Appl. No.: 89,981

[22] Filed: Aug. 27, 1987

[51] Int. Cl.⁴ ............................................. B01D 15/08
[52] U.S. Cl. ............................................. 55/18; 55/67; 55/197; 55/270; 55/386; 210/639; 210/668
[58] Field of Search ............... 55/67, 197, 386, 16, 55/18, 19, 74, 158, 159, 270, 274, 210, 218, 387; 210/638, 639, 644, 668, 745

[56] References Cited

U.S. PATENT DOCUMENTS

| | | | |
|---|---|---|---|
| 2,752,309 | 6/1956 | Emmons et al. | 210/668 |
| 2,843,138 | 7/1958 | Gilman | 210/743 X |
| 3,097,076 | 7/1963 | Reid | 210/638 X |
| 3,431,201 | 3/1969 | Johnson et al. | 210/638 |
| 3,463,615 | 8/1969 | Sochor | 55/386 X |
| 3,468,796 | 9/1969 | Noll et al. | 210/644 X |
| 3,495,943 | 2/1970 | Kapff | 210/638 X |
| 3,749,646 | 7/1973 | Pirt | 210/644 X |
| 3,842,000 | 10/1974 | Dawson | 210/668 |
| 3,927,978 | 12/1975 | Wasik | 55/67 X |
| 3,934,193 | 1/1976 | Hall | 324/30 B |
| 4,032,296 | 6/1977 | Hall | 73/23.1 X |
| 4,233,397 | 11/1980 | Tada et al. | 210/644 X |
| 4,276,177 | 6/1981 | Smith | 210/638 |
| 4,306,946 | 12/1981 | Kim | 210/644 X |
| 4,332,685 | 6/1982 | Nowlin et al. | 210/638 |
| 4,555,383 | 11/1985 | Hall | 422/89 |
| 4,649,124 | 3/1987 | Hall | 436/150 |
| 4,740,309 | 4/1988 | Higuchi | 210/644 |
| 4,758,347 | 7/1988 | Henz et al. | 210/639 |

FOREIGN PATENT DOCUMENTS

| | | | |
|---|---|---|---|
| 2224411 | 10/1974 | France | 210/638 |
| 19148 | 2/1978 | Japan | 210/743 |

OTHER PUBLICATIONS

Piringer, et al., "A New Detector for Gas Chromatography", Journal of Chromatography, vol. 8, pp. 410–412 (1962).

Coulson, Dale M., "Selective Detection of Nitrogen Compounds in Electrolytic Conductivity Gas Chromatography", Journal of Gas Chromatography, pp. 285–287 (Aug. 1966).

Patchett, Gilbert G., "Evaluation of the Electrolytic Conductivity Detector for Residue Analyses of Nitrogen-Containing Pesticides", Journal of Chromatographic Science, vol. 8, pp. 155–158 (1970).

Hall, Randall C., "Optimization and Evaluation of a Microelectrolytic Conductivity Detector for the Gas Chromatographic Determination of Pesticide Residues", Environmental Protection Agency, Grant No. 68-02-1703, Jul. 15, 1975.

Selucky, M. L., "Specific Gas Chromatography Detectors", Chromatographia, vol. 4, pp. 425–434 (1971).

Selucky, M. L., "Specific Gas Chromatography Detectors, Part II: Electrolytic Conductivity Detector", Chromatographia, vol. 5, pp. 359–366 (1971).

Jones, et al., "Versatile Electrolytic Conductivity Detector for Gas Chromatography", Journal of Chromatography, vol. 73, pp. 19–28 (1972).

Hall, Randall C., "A Highly Sensitive and Selective Microelectrolytic Conductivity Detector for Gas Chromatography", Journal of Chromatographic Science, vol. 12, pp. 152–160 (1974).

(List continued on next page.)

Primary Examiner—Robert Spitzer
Attorney, Agent, or Firm—Richards, Harris, Medlock & Andrews

[57] ABSTRACT

A simplified, single component resin bed is coupled with a permeation tube and bottle. The permeation bottle contains an ionic species and a dissolved gas. The apparatus makes unnecessary a multi-component resin ion exchange column for solvent pH control in electrolytic conductivity detection as applied to gas chromatography.

16 Claims, 4 Drawing Sheets

OTHER PUBLICATIONS

Lawrence, et al., "Modified Electrolytic Conductivity Detector Cell for Gas Chromatography", *Analytical Chemistry*, vol. 46, No. 6, pp. 755–757 (1974).

Pape, et al., "The Electrolytic Conductivity Detector as an Element-Selective Gas Chromatographic Detector", *Journal of Chromatography*, vol. 134, pp. 1–24 (1977).

Hall, Randall C., "The Nitrogen Detector in Gas Chromatography", *CRC Critical Reviews in Analytical Chemistry*, Dec. 1978.

Cox, et al., "Dual Ion-Exchange Method for the Controlled Addition of a Prescribed Ionic Species to a Solution", *Analytical Chemistry*, vol. 57, pp. 385–387 (1985).

Pankow, et al., "Adsorption/Thermal Desorption with Small Cartridges for the Determination of Trace Aqueous Semivolatile Organic Compounds", *Analytical Chemistry*, vol. 60, pp. 40–47 (1988).

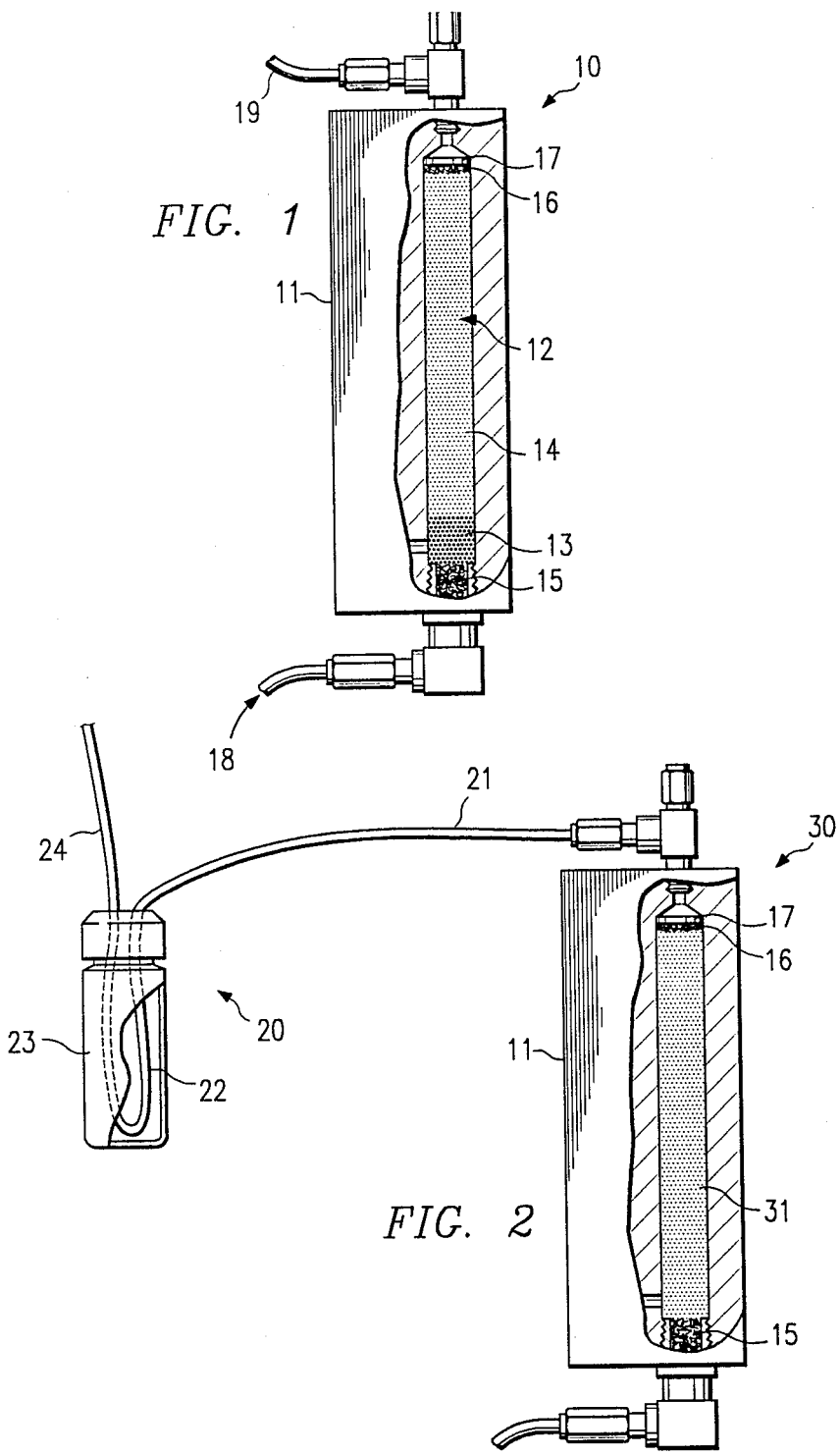

PERMEATION PH CONTROL SYSTEM

FIELD OF THE INVENTION

The present invention pertains to pH control systems and more particularly to a control system adapted to the maintenance of solvent pH in an electrolytic conductivity detector apparatus.

BACKGROUND OF THE INVENTION

The electrolytic conductivity detector was originally reported by Piringer and Pascalau in the Journal of Chromatography, volume 8, p. 410, 1962. By combusting a sample in a furnace containing a CuO catalyst, that sample was converted to carbon dioxide. The carbon dioxide was subsequently dissolved in deionized water and the conductivity of the water was constantly monitored. Similarly, Coulson extended this theory of operation to include the selective detection of halogen, sulfur, and nitrogen containing compounds as described in the Journal of Gas Chromatography, volume 73, p. 19, 1972. Further improvements have been claimed in: Journal of Chromatography, volume 73, p. 19, 1972; Journal of Chromatographic Science, volume 12, p. 152, 1972; Analytical Chemistry, volume 46, p. 755, 1974; Analytic Chemistry, volume 46, p. 755, 1974; Analytic Chemistry, volume 47, p. 367, 1975; U.S. Pat. No. 3,934,193, 1976; U.S. Pat. No. 4,032,296, 1977; NTIS pp. 250 451/256, 1976; U.S. Pat. No. 4,555,383, 1985, U.S. Pat. No. 4,649,124, 1987. Electrolytic conductivity detectors in general are reviewed by Selucky in Chromatographia, volume 5, p. 359, 1972, and specifically for nitrogen detection by Hall in CRC Critical Reviews in Analytical Chemistry, p. 323, 1978.

The importance of proper solvent pH of electrolytic conductivity detectors has been documented by Patchett in Journal of Chromatographic Science, volume 8, p. 155, 1969; Coulson in the Journal of Gas Chromatography, p. 258, 1966; and Pape, et al. in The Journal of Chromatography, volume 134, p. 1, 1977. If, in the nitrogen mode, the pH of the electrolyte is below 7, a decrease in response, "w" shaped peaks, and negative peaks have been observed. For this reason, Selucy in Chromatographia, volume 5, p. 323, 1978, and Jones, et al. in the Journal of Chromatography, volume 73, p. 19, 1972, have claimed that the pH of the solvent should be maintained between 7.0 and 8.0.

Maintenance of solvent pH for the nitrogen mode is usually accomplished through mixed bed resins. Most often, a strong mixed resin bed is preceded by a small amount of a strong base resin of the amine or hydroxyl type. Pape, Rodgers, and Flynn, however, in The Journal of Chromatography, volume 134, p. 1, 1977, have suggested the introduction of nitrogen into the reaction gas stream by means of a mixing manifold as a means of controlling pH.

Mixed bed resins, while controlling the pH to some extent, optimizing peak shape and sensitivity, suffer in actual operation. The final pH of the solvent with these types of systems is highly dependent on flow rate through the bed. This property is used to advantage by Pape, Rodgers, and Flynn in The Journal of Chromatography, volume 134, pp. 1-24, 1977, who use this dependency as the controlling factor in pH adjustment. Having a set flow rate through the resin bed, however, reduces the flexibility in application to differing cell designs and operational techniques. Furthermore, the flow rate needed to maintain a specific pH is not constant over an extended period of time. Cox and Tanaka, in Analytical Chemistry, volume 57, p. 385, 1985, have shown that the ion exchange rate of a resin bed depends on both the ionic content of the incoming solvent and the degree of ionic depletion of the resin bed.

In addition, the two component resin system is harder to prepare than a single component resin system.

SUMMARY OF THE INVENTION

The invention is an improved solvent pH control system for electrolytic conductivity detection in gas chromatography. A simplified, single component resin bed is coupled with a permeation system.

The basic components are the ion exchange resin cartridge filled with a single component resin, the permeation tube, and the permeation bottle. The permeation bottle is filled with an ionic species, which, when added to the solvent through permeation, to the interior of the tubing (such as TEFLON brand), will result in the desired control of solvent pH and remove the necessity for multi-component resin configurations in the ion exchange resin cartridge. One example is the use of an ammonia mixture in the permeation bottle which shifts the pH upward, allowing proper operation with conventional single component resin mixtures in the ion exchange resin cartridge.

BRIEF DESCRIPTION OF THE DRAWINGS

FIG. 1 is a side elevation in partial cross-section of a conventional ion exchange system used in electrolytic conductivity detectors;

FIG. 2 is a side elevation in partial cross-section of the improved ion exchange system and gas permeation apparatus of the present invention;

DESCRIPTION OF THE INVENTION

Figure 3:
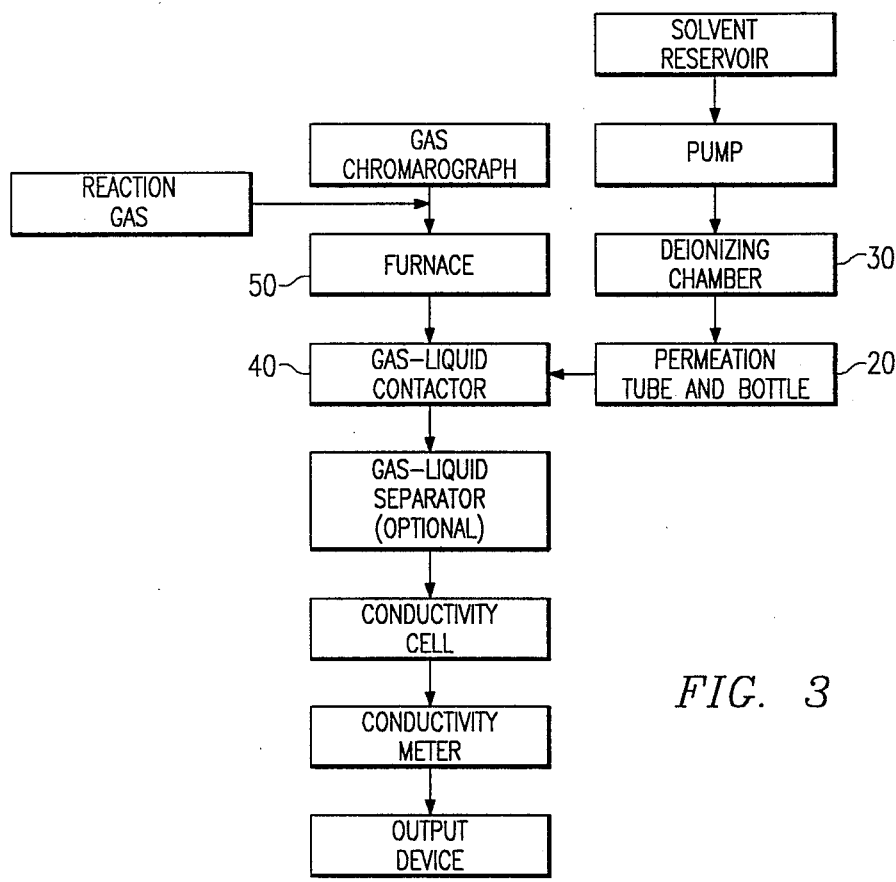
FIG. 3 is a chart illustrating how the permeation tube and bottle are utilized with the improved deionizing chamber in an electrolytic conductivity detector system.

FIG. 1 depicts a conventional ion exchange system 10. A chamber 11 has a column of resin 12 within. In the nitrogen mode a strong base resin 13 and strong mixed resin 14 are contained in the column by glass wool 15, 16. A filter disc 17 is used with the glass wool. Solvent enters the column at an inlet 18 exits at an outlet 19.

The permeation tube and bottle 20 of the present invention are utilized in an electrolytic conductivity detector as shown in FIG. 2. The permeation tube receives the output of a simplified and improved ion exchange system 30. Rather than a multi-component resin system, the present invention employs a simplified ion exchange column, in this instance a single component resin 31. Single component resin beds are inherently more stable in pH of fluid output irrespective of resin life or fluid flow rate. The output of solvent from the ion exchange system flows through a tube 21 made from TEFLON brand material. A length of this tube 22 is contained within the permeation bottle 23. The permeation bottle is filled with a chemical species which sets up an equilibrium between its ionic and gaseous forms. In the case of the nitrogen mode, an ammonium hydroxide solution is used, with the two species in equilibrium being $NH_4+$ and $NH_3$. Because $NH_3$ is a dissolved gas, it permeates the tubing and acts on the solvent to effect a favorable regulation of the solvent pH.

From the output 24 of the permeation bottle, the pH-adjusted solvent enters the gas-liquid contactor 40, where the solvent is reacted with the output of the furnace 50 in the form of combustion products. A schematic of this combination is shown in FIG. 3.

Performance of the solvent pH control system was evaluated with the use of an O.I Corporation Model 4420 Electrolytic Conductivity Detector and a Hewlett Packard Model 5890 Gas Chromatograph. By injecting nitrogen-containing compounds directly onto a capillary column, peak shape and response as a function of solvent pH via permeation could be evaluated. A hexane solution containing 1000 parts per billion of atrazine was used for the peak shape evaluation. Atrazine, having the chemical formula $C_8H_{14}ClN_5$, is considered typical of compounds containing organic nitrogen.

Figure 4A:
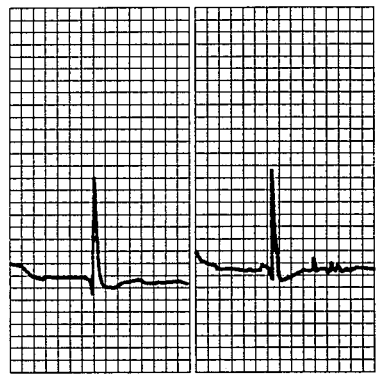
FIGS. 4a–d illustrate in graphic form, the performance of the system, using an atrazine sample, and varying the concentration of the permeation liquid.
Figure 4B:
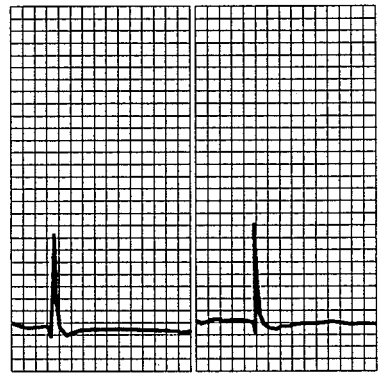
Figure 4C:
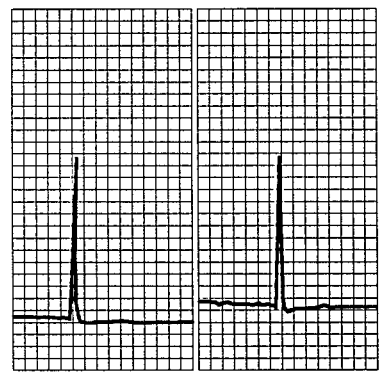
Figure 4D:
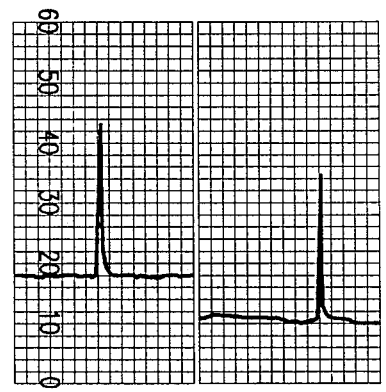
Figure 5A:
FIGS. 5a–d illustrate in graphic form, the performance of the system using a more dilute atrazine sample, again varying the concentration of the permeation liquid.
Figure 5B:
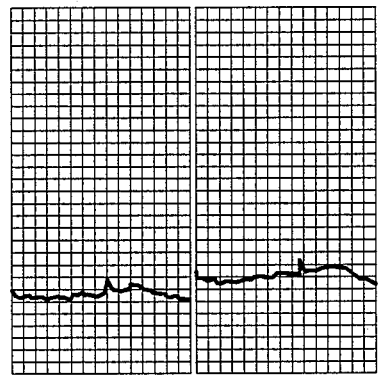
Figure 5C:
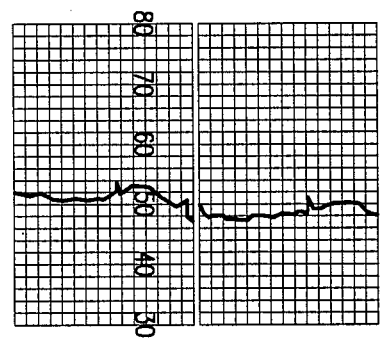
Figure 5D:
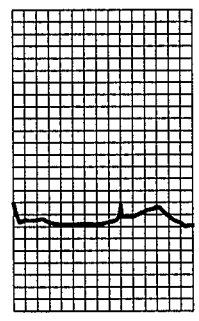

Response of the electrolytic conductivity detector to variations in permeation liquid concentration is shown in FIGS. 4a, 4b, 4c and 4d. In FIG. 4a, there was only water (with 2% hexyl alcohol added for surfactant) in the permeation bottle. Notice the characteristic "W" shaped peak indicating improper pH balance of the conductivity solvent. In FIG. 4b, a solution of ammonium hydroxide, prepared by mixing 0.5 ml of stock ammonia solution (assayed at 30% $NH_3$) to 100 ml of the water/hexyl alcohol solution, was used as the permeation liquid. There is a slight improvement in peak shape, baseline noise, and sensitivity. Further improvement was obtained with 1 ml/100 ml ammonia solution in FIG. 4c and with 1.5 ml/100 ml ammonia solution in FIG. 4d.

Dropping the analyte concentration injected to 0.1 parts per million atrazine, FIGS. 5a, 5b, 5c, and 5d show that further increases in ammonia concentration in the permeation fluid results in no further change in response. FIGS. 5a, 5b, 5c, and 5d illustrate the response of 0.1 parts per million atrazine to 2, 3, 4, and 5 ml/100 ml of this ammonia solution. The results illustrated in FIGS. 5a-d indicate that 2 ml/100 ml represents an optimum ammonia concentration in the nitrogen mode.

Just as the permeation system is benefical in the nitrogen mode, the principles of permeation pH control have applications to other solvent systems. For example, in the halogen mode, dilute weak acid replaces the dilute base as the permeation liquid.

While the principles of the present invention have been described in connection with specific process steps and apparatus, it is to be understood that this description is made only by way of example and not as a limitation to the scope of the invention as set forth in the accompanying claims.

What is claimed is:

1. A method of solvent pH control in an electrolytic conductivity detector, the method comprising:
    passing solvent from a source thereof through a deionizing chamber;
    passing the solvent from the deionizing chamber through a permeation system; and
    introducing the solvent from the permeation system into a gas-liquid contactor, wherein sample gas is contacted with solvent that has passed through the permeation system.

2. The method of claim 1, wherein:
    the deionizing chamber has contained therein a single component ion exchange resin.

3. The method of claim 1 or 2, wherein:
    the permeation system comprises a permeable tube at least partially contained within a permeation bottle, the bottle further containing a permeation liquid.

4. A method in accordance with claim 2, wherein the step of passing the solvent from the deionizing chamber through a permeation system comprising:
    passing said solvent from the deionizing chamber in contact with a first side of a permeable wall having first and second sides; and
    contacting the second side of said permeable wall with a liquid having a pH modifying component which can penetrate said permeable wall.

5. A method in accordance with claim 4, wherein said liquid is a base.

6. A method in accordance with claim 4, wherein said liquid is an acid.

7. A method in accordance with claim 4, wherein said liquid contains an equilibrium of a soluble gas and an ion.

8. A method in accordance with claim 7, wherein said liquid comprises an ammonium hydroxide solution, and wherein said gas is $NH_3$ and said ion is $NH_4+$.

9. In an electrolyte detector apparatus having a supply of solvent which is delivered to a solvent input of a gas-liquid contactor, a solvent pH controlling device comprising:
    an ion exchange column adapted to receive the solvent prior to its delivery to said solvent input of the gas-liquid contactor, said ion exchange column having an output;
    a permeation bottle;
    a tube which is permeable to a soluble gas dissolved in a permeation liquid, the tube leading from said output of the ion exchange column to said permeation bottle;
    the permeation bottle being adapted to contain the permeation liquid, the liquid having in equilibrium the soluble gas and an ion of the soluble gas, the tube passing through the permeation liquid and then attaching to said solvent input of the gas-liquid contactor.

10. The apparatus of claim 9, wherein:
    the ion exchange column contains a single component ion exchange medium.

11. In an electrolytic conductivity detector apparatus having a gas-liquid contactor with a solvent input, a solvent pH controlling device comprising:
    a single component ion exchange column having an input adapted to receive solvent and an output;
    a length of tubing extending between the output of said single component ion exchange column and the solvent input of said gas liquid contactor;
    a permeation container having therein a liquid and specified length of the tubing; and
    the tubing passing through the liquid, the liquid having in equilibrium a soluble gas and an ion of the soluble gas, at least a portion of said specified length of the tubing being permeable to said gas.

12. In conjunction with an electrolytic conductivity detector, a solvent pH controlling system intermediate a solvent supply and a gas-liquid contactor, said system comprising:

an ion exchange column adapted to receive solvent from said solvent supply, the column containing a single component resin, the column having an output in the form of solvent, means for permeation pH control, and means for passing the solvent from said column through said means of permeation pH control to said gas-liquid contactor, thereby controlling the pH of the solvent passing to said gas-liquid contactor.

13. In conjunction with an instrument having a solvent inlet and requiring a flow of pH stabilized solvent through said solvent inlet, a solvent pH controlling device comprising:

a single component ion exchange column having an inlet and an outlet;

a length of tubing having an inlet and an outlet, the inlet of said tubing being affixed to the outlet of said single component ion exchange column, the outlet of said tubing being affixed to said solvent inlet, a portion of the tubing passing through a liquid having in equilibrium a dissolved gas and an ion of the gas, said portion of the tubing being permeable to said gas.

14. The pH controlling device of claim 13, wherein: the liquid is a dilute base.

15. The pH controlling device of claim 13, wherein: the liquid is a dilute acid.

16. The pH controlling device of claim 13 wherein the liquid is an ammonium hydroxide solution.

* * * * *

UNITED STATES PATENT AND TRADEMARK OFFICE
CERTIFICATE OF CORRECTION

PATENT NO. : 4,917,709

DATED : April 17, 1990

INVENTOR(S) : Randall C. Hall, et al.

It is certified that error appears in the above-identified patent and that said Letters Patent is hereby corrected as shown below:

Column 2, line 54, after "18" insert --and--.

Column 4, line 28, change "electrolyte" to --electrolytic--.

Signed and Sealed this

Eleventh Day of June, 1991

Attest:

HARRY F. MANBECK, JR.

Attesting Officer

Commissioner of Patents and Trademarks